United States Patent [19]
Caudillo et al.

[11] Patent Number: 5,906,642
[45] Date of Patent: May 25, 1999

[54] UNIVERSAL HEART VALVE HOLDER

[75] Inventors: Roberto Caudillo; Tammi E. Klostermeyer, both of Austin; James C. Caffey, Marble Falls, all of Tex.

[73] Assignee: Sulzer Carbomedics Inc., Austin, Tex.

[21] Appl. No.: 08/989,843

[22] Filed: Dec. 12, 1997

[51] Int. Cl.⁶ ........................................... A61F 2/24
[52] U.S. Cl. ................... 623/2; 623/900; 606/1
[58] Field of Search ................ 623/2, 166, 900; 606/1

[56] References Cited

U.S. PATENT DOCUMENTS

| | | | |
|---|---|---|---|
| 4,655,218 | 4/1987 | Kulik et al. | 623/2 |
| 5,522,884 | 6/1996 | Wright | 623/2 |
| 5,582,607 | 12/1996 | Lackman | 606/1 |
| 5,669,919 | 9/1997 | Sanders et al. | 606/148 |
| 5,682,906 | 11/1997 | Sterman et al. | 128/898 |
| 5,713,951 | 2/1998 | Garrison et al. | 623/2 |
| 5,716,370 | 2/1998 | Williamson, IV et al. | 606/153 |
| 5,716,398 | 2/1998 | Sparks et al. | 623/2 |
| 5,716,401 | 2/1998 | Eberhardt et al. | 623/2 |
| 5,716,402 | 2/1998 | Reif | 623/2 |
| 5,718,725 | 2/1998 | Sterman et al. | 623/2 |
| 5,735,842 | 4/1998 | Krueger et al. | 606/1 |
| 5,735,894 | 4/1998 | Krueger et al. | 623/2 |

FOREIGN PATENT DOCUMENTS

| | | | |
|---|---|---|---|
| 0878285 | 11/1981 | U.S.S.R. | 623/2 |
| 092012688 | 8/1992 | WIPO | 623/2 |

Primary Examiner—Mickey Yu
Assistant Examiner—Dinh X. Nguyen
Attorney, Agent, or Firm—Philip S. Lyren; Kenneth S. Barrow

[57] ABSTRACT

A heart valve holder is provided for implanting a prosthetic heart valve in either an inflow (mitral or tricuspid) or an outflow (aortic or pulmonary) implantation. The valve holder may be repeatedly sterilized for multiple implantations. The valve holder includes holding members to securely hold the valve, a valve-sizing member to allow the holder to hold valves of various sizes, an over rotation stop to prevent the holder from impinging upon the valve leaflets, alignment members to align the holding members for receiving a valve, and means to rotate the valve without damaging the valve leaflets.

27 Claims, 6 Drawing Sheets

UNIVERSAL HEART VALVE HOLDER

BACKGROUND OF THE INVENTION

The present invention relates to surgical devices, namely, a device for selectively holding and positioning a prosthetic heart valve for implantation.

A prosthetic heart valve is used to replace a native heart valve that is malformed, damaged, or otherwise unable to properly regulate blood flow through a heart. Typically, a prosthetic heart valve includes a generally annular, rigid ring supporting one or more leaflets. The leaflets open and close to regulate blood flow in one direction. The mitral and tricuspid valves function as "inflow" valves, i.e., regulate blood flow into the ventricles, thus preventing backflow into the auricles. The aortic and pulmonary valves function as "outflow" valves, i.e., regulate blood flow out of the ventricles, thus preventing backflow into the ventricles.

A valve holder is used by a surgeon to hold and position a prosthetic heart valve for attachment to the native valve annulus, and sometimes to turn the valve body after the valve is placed within the heart to orient the leaflets away from potential contact with surrounding tissue. Although a single type of prosthetic heart valve may be used for either inflow or outflow valve replacement, the valve holder must grasp the valve from the proper end of the valve, so that the leaflets are properly oriented (inflow or outflow) for the designated type of implantation. Also, prosthetic valves are manufactured in different sizes, allowing a surgeon to select the valve size which is closest to the size of the native annulus receiving the valve. The valve holder must be carefully manipulated by the surgeon in order to prevent any stress or damage to the valve leaflets.

Many prosthetic heart valves are provided with pre-attached, disposable valve holders. Consequently, the valve holder is matched with a valve for size and orientation. However, this configuration adds to the total cost of the valve and creates additional medical waste (the valve holder) which must be properly disposed. Also, the pre-attached valve holder predisposes the use of the valve as either an inflow or outflow valve, increasing the inventory of prosthetic valve/holder combinations a hospital carries.

Another holder configuration employs a single handle which may be coupled with one of three different attachments for various valve sizes. Refer generally to Morse, Dryen, et al., *Guide to Prosthetic Cardiac Valves*, Springer-Verlag, 1985. This configuration also has the drawback of the cost and inventory for each of the attachments.

SUMMARY OF THE INVENTION

The present invention is directed to a universal heart valve holder for holding and positioning a prosthetic heart valve during implantation. The universal valve holder includes first and second arms that are coupled at their respective proximal ends. The coupling forms a spring between the two arms so that the distal ends of the arms are selectively movable toward each other. A valve contact shoe is positioned at the distal end of each arm. Each shoe includes an upper and lower lip, and a generally curved central body, for positioning between the leaflets and annular ring of a heart valve. The curved central body of each shoe roughly conforms to the inner curvature of the valve ring. When the shoes are inserted into a valve and tension on the arms is released, the shoes engage the valve ring, and the lips prevent the valve ring from sliding off of the shoes. Therefore, the valve is firmly coupled with the holder and a surgeon may position the valve by manipulating the holder. The shoes allow the valve to be grasped from either end, thereby allowing a valve to be used as either an inflow or an outflow valve. Also, the holder is used to rotate the valve body and leaflets after the valve is placed within the heart.

A valve-sizing member is coupled with and extends generally orthogonal to one of the arms. The valve-sizing member is selectively rotatable to couple with the other arm, thereby locking the distance between the distal ends of the two arms. Once a surgeon has positioned the shoes in a valve, the valve-sizing member is used to lock the arms in place. Also, the surgeon is less likely to drop the valve from the holder by inadvertently placing pressure on the arms. The valve-sizing member includes a plurality of keys for coupling with the second arm. Each key defines a distance between the two arms corresponding to distance between the two shoes necessary to hold a valve for a given valve size or range of sizes. Therefore, selective use of the keys allows the valve holder to be used with numerous valve sizes.

An arm rotation stop is positioned on at least one of the arms in a medial portion of the arm. The rotation stop extends generally orthogonal to the longitudinal axis of the arm and toward the second arm. The stop limits the distance which the arms may be rotated toward each other during the process of grasping the valve so that the shoes or distal ends of the arms cannot impinging upon and possibly damage the valve leaflets. In another embodiment, rotation stops are positioned on both arms.

Alignment members are positioned toward the distal ends of each arm. The alignment members interlock, serving to align the two arms relative to each other so that the shoes are aligned. This alignment ensures that the valve is properly grasped by the shoes. In one embodiment, the alignment members include a configuration of diagonal posts and diagonal recesses. The post/recess configuration on the arms is such that the posts on one arm align with the recesses on the other arm. When the arms are rotated toward each other so that the posts fit into the recesses, the shoes of each arm are properly aligned relative to each other.

Finger pads may be positioned on the medial section of each arm, providing a surgeon with a generally flat or concave, non-slip surface for controlling the two arms. The components of the valve holder are made of biocompatible and repeatedly sterilizable materials so that the holder may be used for numerous implantation procedures. The combination of these features results in a universal prosthetic valve holder for all or many valve sizes, which reduces inventory and waste, lowers costs, allows a valve to be used as either an inflow or outflow valve, and reduces the risk of valves being damaged or dropped during implantation.

DETAILED DESCRIPTION OF THE EMBODIMENTS

Figure 1:
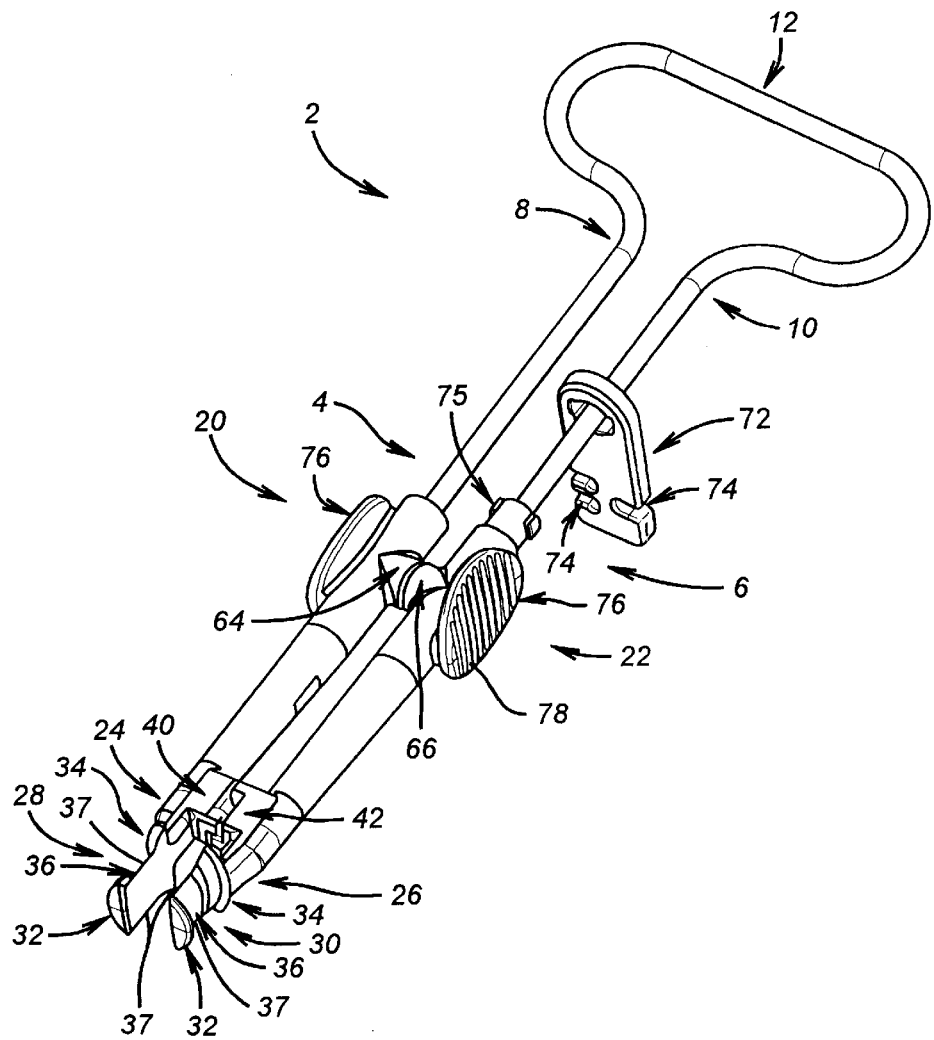
FIG. 1 is a perspective view of a valve holder.
Figure 2:
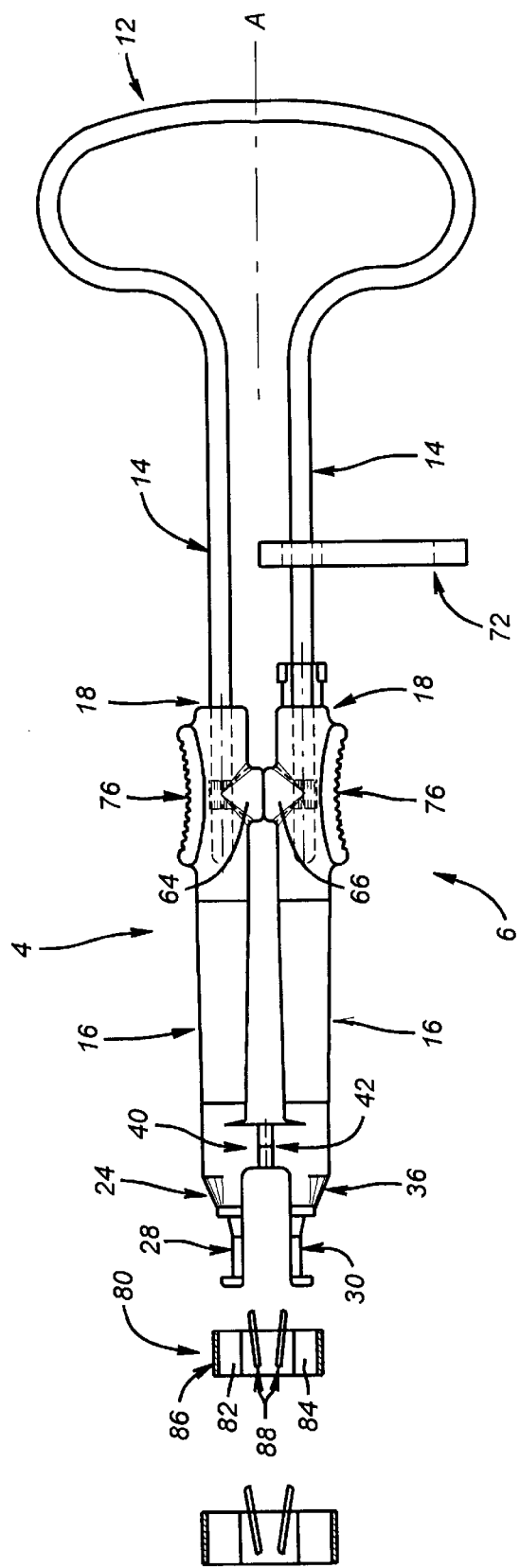
FIG. 2 is a top view of a valve holder.

A universal valve holder according to the invention is shown in FIG. 1. Valve holder 2 includes a first arm 4 and a second arm 6 coupled at their respective proximal ends 8, 10 by a coupling member 12. Coupling member 12 serves as a spring between arms 4 and 6. In the embodiment shown in FIG. 1, coupling member 12 is generally "U"-shaped. In another embodiment, the proximal ends 8, 10 of arms 4, 6 are coupled directed with each other and biased to form a spring, similar to the configuration of the common tweezers. In the embodiment shown in FIG. 2, arms 4, 6 comprise two components, an upper spring portion 14 and lower, more rigid portion 16. The portions 14, 16 may be threaded to screw together, or are otherwise securely coupled together by glue, friction fit or other means at coupling 18. In one embodiment, coupling member 12 biases arms 4, 6 about eight degrees from a centerline A when no load is applied to the arms. (FIGS. 1 and 2 show arms 4, 6 in a fully flexed position.)

First and second arms 4, 6 and coupling member 12 are made from a spring material which may be repeatedly sterilized. Consequently, holder 2 may be used for numerous valve implantations. In one embodiment, arms 4, 6 and coupling member 12 are made from stainless steel. Other suitable materials including metal, metal coated with plastic, plastic, or combinations thereof, which may be repeatedly sterilized. Suitable plastic compositions include polysulfone, polycarbonate, polyetherimide, and combinations thereof.

Referring again to FIG. 1, arms 4, 6 are elongate members that include medial sections 20, 22, respectively, and distal ends 24, 26, respectively. In one embodiment, the length of arms 4, 6 from coupling member 12 to the distal ends is about seven inches, and arms 4, 6 are about 0.125 inches thick. Positioned at the distal ends 24, 26 are valve contact shoes 28, 30. Each contact shoe includes a distal lip 32, a proximal lip 34, and a central body 36. The outer surface of central body 36 extending between the lips has a convex curvature to maximize the surface area of shoes 28, 30 which contact the inner surface of a prosthetic valve ring, as discussed further below. Rotation means comprise edges 37 of central body 36, and allows the holder to rotate the valve without damaging the leaflets. The length of each shoe, from distal to proximal lip, is about one-half inch. Shoes 28, 30 are made from biocompatible materials, including metal, metal coated with plastic, plastic, or combinations thereof, which may be repeatedly sterilized.

Figure 3:
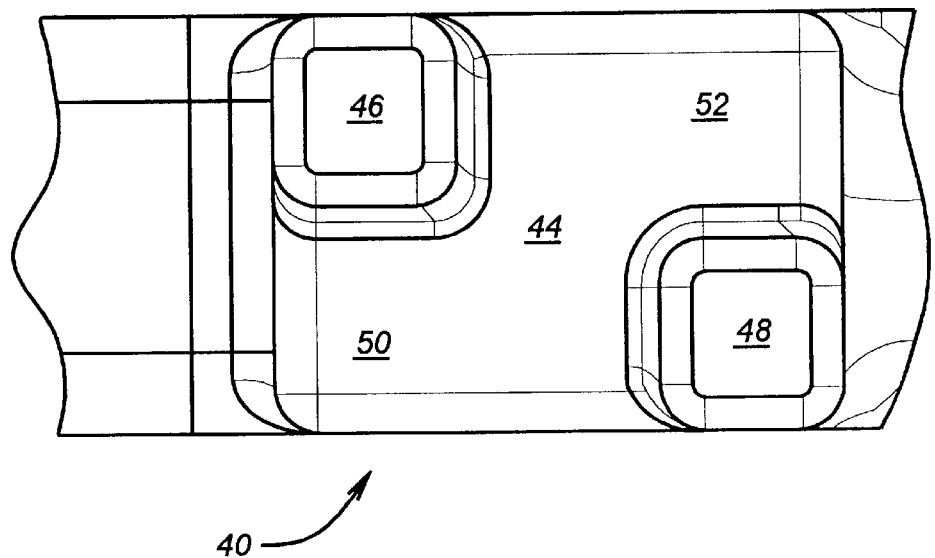
FIG. 3 is a perspective view of an alignment member.

Alignment members 40, 42 are positioned near distal ends 24, 26. As shown in FIG. 3, alignment member 40 includes a face 44. Extending from face 44 are two posts 46, 48 which are positioned generally diagonal from each other. The portions 50, 52 of face 44 opposite posts 46, 48 are generally recessed when compared to posts 46, 48 and form receiving areas. Alignment member 42 is configured in the same manner as alignment member 40, except that the posts, and consequently the receiving areas, are rotated ninety degrees. Therefore, when alignment members 40, 42 are properly aligned and moved into contact with each other, the posts of alignment member 40 contact the receiving areas of alignment member 42, and the posts of alignment member 42 contact the receiving areas of alignment member 40. When alignment members 40, 42 are properly coupled, i.e., the posts fit with the receiving areas, shoes 28, 30 are properly aligned to be positioned in a prosthetic heart valve, as shown in FIGS. 1 and 2. Alignment members 40, 42 are made from biocompatible materials, including metal, metal coated with plastic, plastic, or combinations thereof, which may be repeatedly sterilized.

Referring again to FIG. 1, leaflet protection stops 64, 66 are positioned along the medial sections 20, 22 of arms 4, 6. Leaflet protection stops 64, 66 extend generally orthogonal to the longitudinal axis of arms 4, 6, and toward each other. The length which leaflet stops 64, 66 extend from medial sections 20, 22 is selected so that arms 4, 6 cannot over-rotate toward each other to the extent where shoes 28, 30 can impinge upon the leaflets of a valve to be grasped by valve holder 2. Referring to FIG. 2 as an example, arms 4 and 6 are fully flexed toward each other and leaflet stops 64 and 66 are in contact with each other. Shoes 28, 30 can still pass into valve ring 86 without contacting leaflets 88. Leaflet protection stops 64, 66 are made from biocompatible materials, including metal, metal coated with plastic, plastic, or combinations thereof, which may be repeatedly sterilized. In another embodiment, only one stop is used, extending from either the first or second arm.

Figure 4:
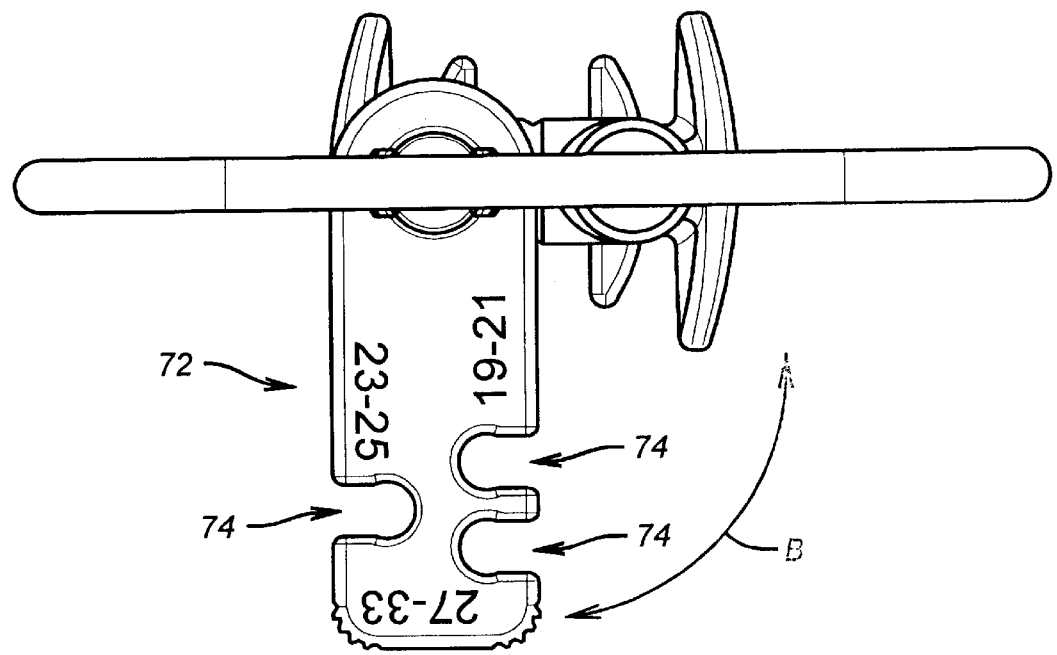
FIG. 4 is a frontal view of a valve retention lock positioned on a valve holder.

A valve retention lock 72 is coupled with either first arm 4 or second arm 6, and is rotatable about the arm to selectively lock onto the other arm (as shown by arrow B in FIG. 4). In the embodiment shown in FIGS. 1 and 2, valve retention lock 72 is coupled with second arm 6. Retention lock 72 is generally planar and includes a plurality of keys or recesses 74 which represent different valve sizes or ranges of sizes. In the embodiment shown in FIG. 4, there are three recesses 74, one representing valves sizes 19–21 mm, one recess representing valves sizes 23–25, and one recess representing valves sizes 27–33. In the embodiment shown in FIG. 1, retention lock 72 is generally slidable along arms 4 and 6, and coupling member 12. When retention lock 72 is to be employed, it is slid over limiting member 75 and rotated toward the other arm. Limiting member 75 holds retention lock 72 in place on the arm. In one embodiment, valve retention lock 72 is made from biocompatible materials, including metal, metal coated with plastic, plastic, or combinations thereof, which may be repeatedly sterilized.

Valve holder 2 may also include finger pads 76, positioned on arms 4, 6, generally opposite leaflet protection stops 64, 66, as shown in FIGS. 1 and 2. Finger pads 76 include an outer surface 78 having ribs or other non-slip surface treatment. Finger pads 76 are made from biocompatible materials, including metal, metal coated with plastic, plastic, or combinations thereof, which may be repeatedly sterilized. Also, arms 4, 6 may be ribbed or include an outer textured surface to assist in grasping the arms.

Figure 5:
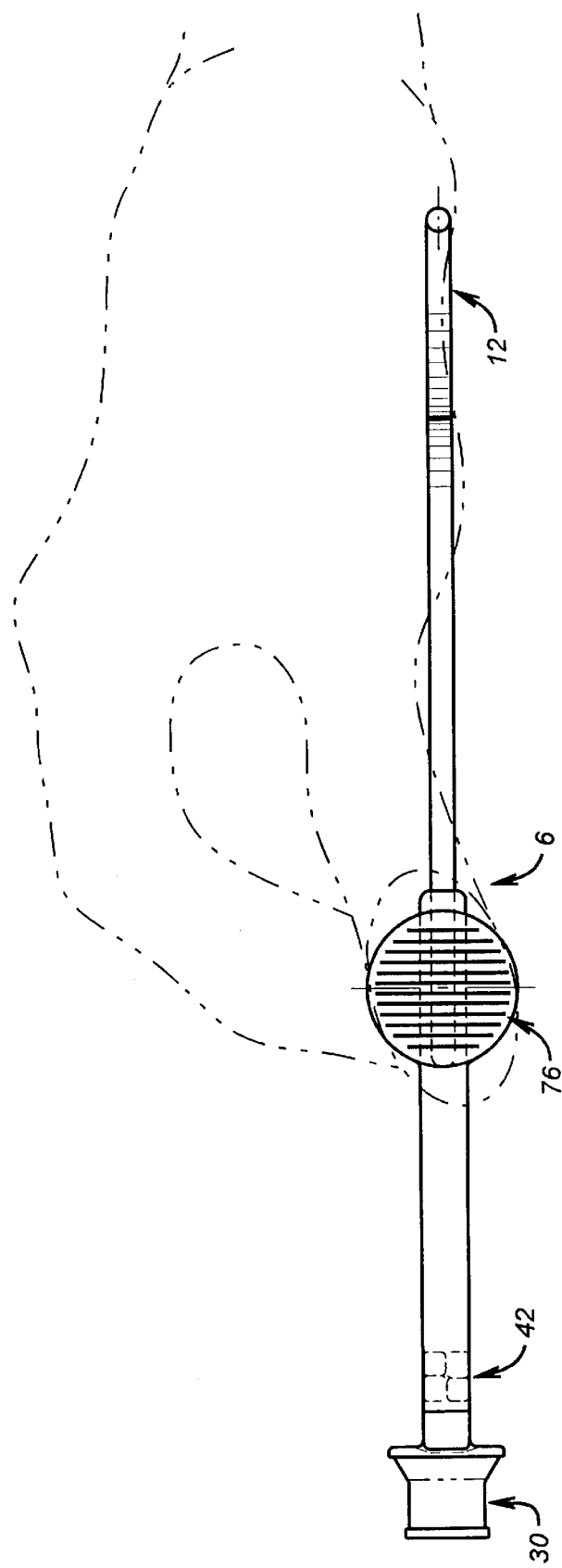
FIG. 5 is an side view of a valve holder being grasped.

When using valve holder 2, a surgeon grasps it, typically by placing thumb and forefinger on finger pads 76, as shown in FIG. 5. By compressing pads 76, coupling member 12 flexes, moving arms 4, 6 toward each other. As shown in FIG. 2, in order to hold a prosthetic heart valve 80, arms 4, 6 are flexed sufficiently so that shoes 28, 30 extend into regions 82, 84, defined by annular ring 86 and leaflets 88 of valve 80. Leaflets 88 are crucial components of prosthetic valve 80 as they are the components that must repeatedly rotate, thereby allowing blood to flow in one direction but not the opposite direction. It is important that when grasping valve 80, a surgeon place no pressure on leaflets 88. With valve holder 2 of the present invention, leaflet protection stops 64, 66 will contact each other before shoes 28, 30 or portions of distal ends 24, 26 can impinge upon leaflets 88. Therefore, when positioning valve holder 2 to grasp valve 80, the surgeon cannot over rotate arms 4, 6 (and possibly damage leaflets 88).

Figure 6:
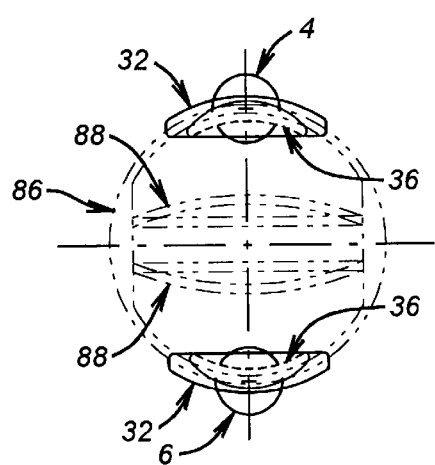
FIG. 6 is an end view of a prosthetic heart valve and the shoes of a valve holder with the shoes positioned on the valve.

The surgeon extends shoes 28, 30 through valve 80 until distal lips 32 extend beyond the distal extent of ring 86, as shown in FIG. 6. Proximal lips 34 extend beyond the proximal extent of ring 86. Once lips 32, 34 are positioned, a surgeon can release the force on arms 4, 6 and valve 80 is seated in shoes 28, 30 and cannot slip out.

Figure 7:
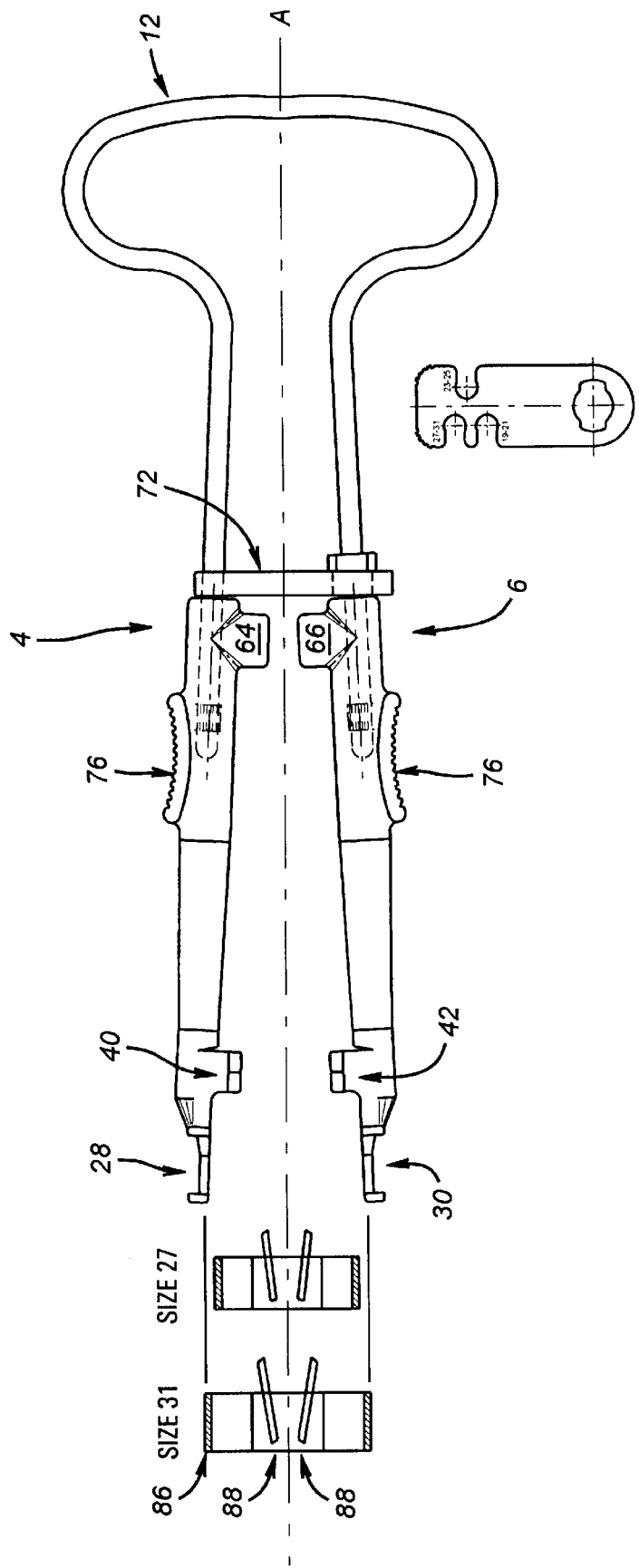
FIG. 7 is a top view of a valve holder with the retention lock in the locked position.

Next, the surgeon rotates retention lock 72 so that the selected recess 74, which matches the size range of valve being implanted, rests around arm 6, thereby locking arms 4, 6. Referring to FIG. 7, retention lock 72 is used to lock arms 4 and 6 in place for holder 2 to hold a 31 mm valve. Also, retention lock 72 serves to prevent accidentally dropping the valve by inadvertently flexing arms 4, 6. The surgeon may then position the valve and holder, move them around, place a force one the arms, all without fear of separating the valve from the holder. Once the valve is positioned and fixed in the native annulus, a surgeon may rotate the valve if necessary, and/or release retention lock 72 and flex arms 4, 6 to allow shoes 28, 30 to move out of the valve through regions 82, 84. Throughout the manipulations of valve holder 2, the leaflets are not damaged by valve holder 2 due to leaflet protection stops 64, 66.

Figure 8:
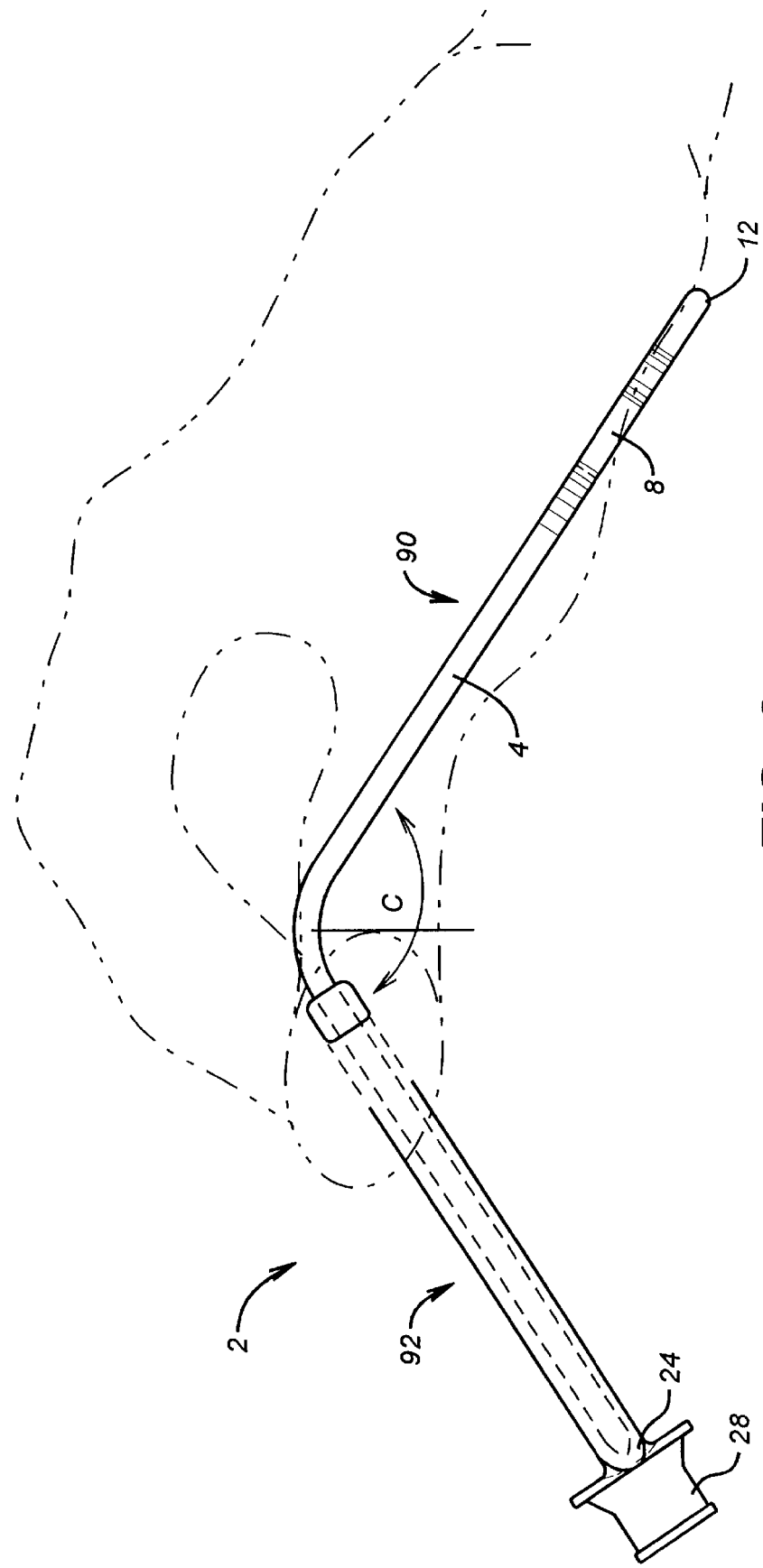
FIG. 8 is a side view of another embodiment of the valve holder.

As shown in FIGS. 1 and 2, arms 4, 6 are generally linear. In the embodiment of FIG. 8, arms 4, 6 include first and second segments, 90, 92, respectively, forming obtuse angle C. In one embodiment angle C is about 130° degrees.

Other embodiments are within the scope of the following claims.

We claim the following:

1. An apparatus for holding a prosthetic heart valve, comprising:
    a first arm having a proximal end, a distal end, and a medial section intermediate the proximal and distal ends;
    a first valve holding member coupled with the distal end of the first arm;
    a second arm having a proximal end, a distal end, and a medial section intermediate the proximal and distal ends;
    a second valve holding member coupled with the distal end of the second arm;
    a coupling member operably attaching the proximal ends of the first and second arms, wherein the arms are adapted to move relative to each other such that the distance between the distal ends is adjustable;
    a valve-sizing member operably coupled with the first arm and selectively coupled with the second arm so that the distance between the first and second arms is selectively fixed;
    an over rotation stop operably coupled with the medial section of the first arm and generally orthogonal thereto, thereby limiting the extent to which the distal ends may be moved toward each other; and
    a first alignment member operably coupled with the first arm and a second alignment member operably coupled with the second arm, wherein the alignment members interlock when the distal ends are moved toward each other, thereby aligning the valve holding members to receive a prosthetic heart valve.

2. The apparatus of claim 1 wherein the first and second arms comprise a flexible material.

3. The apparatus of claim 1 wherein the first and second arms each include a first and a second segment.

4. The apparatus of claim 3 wherein the first and second segments are positioned at an obtuse angle relative to each other.

5. The apparatus of claim 1 wherein the first and second valve holding members include a first lip, a second lip, and a body intermediate the first and second lips.

6. The apparatus of claim 1 wherein the valve sizing member is generally planar and includes a plurality of recessed portions.

7. The apparatus of claim 1 further comprising a second over rotation stop operably coupled with the medial section of the second arm.

8. The apparatus of claim 1 wherein the first and second alignment members include a generally planar surface and a plurality of posts extending from the surface.

9. The apparatus of claim 1 further comprising a first finger pad operably coupled with the first arm and a second finger pad operably coupled with the second arm.

10. The apparatus of claim 1 wherein the valve holder comprises materials that are repeatedly sterilizable.

11. The apparatus of claim 1 wherein the valve holder is adapted to selectively hold inflow or outflow prosthetic heart valves.

12. A prosthetic heart valve holder, comprising:
    first and second generally opposed elongate members operably coupled with each other at respective proximal ends, the elongate members further including distal ends that are selectively movable toward each other by exerting a force on one or both of the elongate members;
    first and second valve contact shoes operably coupled with the distal ends of the respective first and second elongate members;
    a valve retention lock operably coupled with the first elongate member and selectively coupled with the second elongate member, the lock including a plurality of lock keys, providing a plurality of fixed distances between the elongate members;
    a first leaflet protection stop operably coupled with a medial section of the first elongate member, wherein the first stop limits the rotation of the elongate members toward each other; and
    first and second alignment keys positioned toward the distal ends of the respective elongate members, wherein the keys align the valve contact shoes to receive a prosthetic heart valve.

13. The apparatus of claim 12 wherein the valve holder is adapted to selectively hold inflow or outflow prosthetic heart valves.

14. The apparatus of claim 12 wherein the first and second valve contact shoes include a first lip, a second lip, a body intermediate the first and second lips, and an edge for rotating the valve.

15. The apparatus of claim 12 wherein the first leaflet protection stop extends generally orthogonal to the first elongate member.

16. The apparatus of claim 12 further comprising a second leaflet protection stop operably coupled with a medial section of the second elongate member.

17. The apparatus of claim 12 wherein the first and second alignment keys include a generally planar surface and a plurality of posts extending from the surface.

18. The apparatus of claim 12 further comprising a first finger pad operably coupled with the first elongate member and a second finger pad operably coupled with the second elongate member.

19. The apparatus of claim 12 wherein the valve holder comprises materials that are repeatedly sterilizable.

20. A prosthetic heart valve holder, comprising:
    first and second generally opposed elongate members coupled together and having distal ends that are selectively movable toward each other;
    first and second valve contact shoes connected to the distal ends of the respective first and second elongate members; and a valve retention lock coupled to the first elongate member and having a plurality of recessed portions, wherein the valve retention lock is moveable around the first elongate member to selectively couple the recessed portions with the second elongate member to provide a plurality of fixed distances between the first and second valve contact shoes.

21. The prosthetic heart valve holder of claim 20 in which:

the valve retention lock has an elongated planar configuration; and the recesses are located around the periphery of the valve retention lock and have a semi-circular shaped portion to engage the second elongate member.

22. The prosthetic heart valve holder of claim 20 in which:

the valve retention lock has first, second, and third recesses;

the first recess separates the first and second valve contact shoes a distance sufficient to engage the prosthetic heart valve having a size of about 19–21 mm;

the second recess separates the first and second valve contact shoes a distance sufficient to engage the prosthetic heart valve having a size of about 23–25 mm; and the third recess separates the first and second valve contact shoes a distance sufficient to engage the prosthetic heart valve having a size of about 27–33 mm.

23. A prosthetic heart valve holder, comprising:

first and second elongate members coupled together and having distal ends that are selectively movable toward each other;

first and second valve contact shoes attached to the distal ends of the respective first and second elongate members; and first and second alignment members positioned toward the distal ends of the respective elongate members and having at least one generally planar receiving area and at least one post to align the valve contact shoes, wherein the post of the first alignment member engages the receiving area of the second alignment member and the post of the second alignment member engages the receiving area of the first alignment member.

24. The heart valve holder of claim 23 in which the first and second alignment members include two receiving areas and two posts.

25. The heart valve holder of claim 24 in which:

the first and second alignment members have a rectangular configuration;

the two posts for each first and second alignment member are located in opposite corners of the rectangular configuration; and the two receiving areas for each first and second alignment member are located in opposite corners of the rectangular configuration.

26. A prosthetic heart valve holder, comprising:

first and second elongate members coupled together and having distal ends that are selectively movable toward each other;

first and second valve contact shoes connected to the distal ends of the respective first and second elongate members;

first and second alignment members positioned toward the distal ends of the respective elongate members; and first and second leaflet stops coupled with the first and second elongate members respectively, wherein the first and second leaflet stops extend orthogonally from the first and second elongate members respectively, and the first and second leaflet stops are disposed oppositely from each other, and the first and second leaflet stops limit the rotation of the elongate members toward each other.

27. The prosthetic heart valve holder of claim 26 in which:

the first and second leaflet stops have a cylindrical configuration with circular ends; and the ends of the first and second leaflet stops abut each other to limit the rotation of the elongate members toward each other.

* * * * *